(12) United States Patent
Peng et al.

(10) Patent No.: US 11,786,654 B2
(45) Date of Patent: Oct. 17, 2023

(54) FIELD FIRST-AID INFUSION DEVICE FOR FRIGID HIGHLAND ZONES

(71) Applicant: The Third Medical Center of the Chinese People's Liberation Army General Hospital, Beijing (CN)

(72) Inventors: Bibo Peng, Beijing (CN); Shengnan Li, Beijing (CN); Jing Guo, Beijing (CN); Lina An, Beijing (CN)

(73) Assignee: The Third Medical Center of the Chinese People's Liberation Army General Hospital, Beijing (CN)

( * ) Notice: Subject to any disclaimer, the term of this patent is extended or adjusted under 35 U.S.C. 154(b) by 0 days.

(21) Appl. No.: 17/849,059

(22) Filed: Jun. 24, 2022

(65) Prior Publication Data

US 2023/0166028 A1    Jun. 1, 2023

(30) Foreign Application Priority Data

Nov. 29, 2021    (CN) .......................... 202111432778.6

(51) Int. Cl.
*A61M 5/158*    (2006.01)
*A61M 5/44*    (2006.01)
(Continued)

(52) U.S. Cl.
CPC ..... *A61M 5/158* (2013.01); *A61M 2005/1585* (2013.01); *A61M 2205/18* (2013.01);
(Continued)

(58) Field of Classification Search
CPC .... A61B 17/3472; A61F 7/0085; A61M 1/36; A61M 1/3613; A61M 1/3623; A61M 2205/1585; A61M 2202/10; A61M 2205/127; A61M 2205/18; A61M 2205/3331; A61M 2205/3334; A61M 2205/3362; A61M 2205/36; A61M 2205/3633; A61M 2205/3653; A61M 2205/505; A61M 2205/581; A61M 2205/582; A61M 2205/587;
(Continued)

(56) References Cited

U.S. PATENT DOCUMENTS 9,289,546 B2 *    3/2016    Erickson ............. A61M 1/3681
2002/0045857 A1 *    4/2002    Magnusson ........... A61M 5/445
604/113

(Continued)

*Primary Examiner* — Andrew J Mensh
*Assistant Examiner* — Jihad Dakkak
(74) *Attorney, Agent, or Firm* — CALDERON SAFRON & COLE PC; Corinne Marie Pouliquen

(57) ABSTRACT

The invention relates to the technical field of highland first aid, and particularly discloses a field first-aid infusion device for frigid highland zones. The device comprises a storage box, comprising a heat preservation and pressurization device, a marrow cavity puncture needle, a heat preservation infusion tube, a power-assisted puncture tool, a power supply and a power line, the heat preservation and pressurization device is electrically connected with the power supply through the power line, the heat preservation and pressurization device comprises a heating sleeve, magic tape is fixed to the surfaces of the two ends of the heating sleeve, a control box is fixed to the middle of the outer surface of the heating sleeve, and the power line is inserted into the control box.

9 Claims, 8 Drawing Sheets

(51) Int. Cl.
  *A61M 5/14* (2006.01)
  *A61M 5/148* (2006.01)
  *A61M 5/168* (2006.01)
(52) U.S. Cl.
  CPC .............. *A61M 2205/3331* (2013.01); *A61M 2205/3334* (2013.01); *A61M 2205/3368* (2013.01); *A61M 2205/36* (2013.01); *A61M 2205/3653* (2013.01); *A61M 2205/505* (2013.01); *A61M 2205/581* (2013.01); *A61M 2205/582* (2013.01); *A61M 2205/587* (2013.01); *A61M 2205/825* (2013.01); *A61M 2205/8206* (2013.01); *A61M 2205/8293* (2013.01); *A61M 2210/02* (2013.01)
(58) Field of Classification Search
  CPC .... A61M 2205/8206; A61M 2205/825; A61M 2205/8293; A61M 2210/02; A61M 5/14; A61M 5/142; A61M 5/148; A61M 5/158; A61M 5/16877; A61M 5/44; A61M 5/445
  USPC ........................................................ 604/408
  See application file for complete search history.

(56) References Cited

U.S. PATENT DOCUMENTS

| | | | | |
|---|---|---|---|---|
| 2002/0147426 | A1* | 10/2002 | Faries, Jr. | A61M 5/445 604/113 |
| 2005/0252821 | A1* | 11/2005 | Azzolini | A61M 5/1483 128/849 |
| 2006/0196505 | A1* | 9/2006 | Izuchukwu | A61M 16/104 128/203.15 |
| 2007/0084742 | A1* | 4/2007 | Miller | A61B 50/20 206/438 |
| 2008/0277219 | A1* | 11/2008 | McCarthy | A45C 15/00 190/109 |
| 2011/0297147 | A1* | 12/2011 | Lick | A61B 50/31 128/202.16 |
| 2016/0074578 | A1* | 3/2016 | Xu | A61M 5/14244 604/132 |
| 2020/0324042 | A1* | 10/2020 | King | A61M 5/1424 |
| 2021/0178086 | A1* | 6/2021 | Choi | G16H 20/17 |
| 2022/0340856 | A1* | 10/2022 | Black | A01N 1/0263 |

* cited by examiner

FIELD FIRST-AID INFUSION DEVICE FOR FRIGID HIGHLAND ZONES

CROSS REFERENCE TO RELATED APPLICATION AND CLAIM TO PRIORITY

This patent application claims the benefit and priority of Chinese Patent Application No. 202111432778.6, filed on Nov. 29, 2021, the disclosure of which is incorporated by reference herein in its entirety as part of the present application.

FIELD OF THE INVENTION

The disclosure relates to the technical field of first aid in highland zones, in particular to a field first-aid infusion device for frigid highland zones.

BACKGROUND OF THE INVENTION

Intravenous infusion is a technique in which a large amount of liquid, electrolytes or blood can be infused intravenously into the human blood system. According to the differences in injection site and infusion components, the infusion can be divided into peripheral intravenous infusion, central intravenous infusion, Total Parenteral Nutrition (TPN) and blood transfusion. Intravenous infusion is a highly specialized treatment technique which is involved with parenteral infusion, nutritional support, medication, and infusion at the therapeutic level. Reviewing the history, infusion began in the 17th century, and great progress was made into the 20th century. The infusion route was expanded from peripheral small vessels to large veins and bone marrow cavity; the puncture needle was expanded from a common needle to a trocar and an indwelling catheter; and dressings for punctures were expanded from ordinary cotton dressings to dressings with self-adhesive and elastic properties. The infusion environments were expanded from hospitals to out-of-hospital disaster sites, battlefields, ambulances, and medical aircrafts. According to these inventions, the living space of patients is further improved, and the effectiveness of rescue is improved. Intravenous infusion has the unparalleled advantages over oral medication and intramuscular injection medication, including the ease of achieving therapeutic concentrations of drugs and the sustained maintenance of a constant concentration required for therapeutic effect. Drugs irritative to muscle and subcutaneous tissues can be medicated intravenously. In particular, when shock is treated, fluid or blood lost by the body can be quickly replenished. Therefore, intravenous infusion is anti-shock, and is the most fundamental and effective measure to rescue those suffering from shock.

According to the basic requirements for infusing a patient, generally, the patient sits or lies flat in a clean treatment room, superficial veins near the puncture point of the arm or foot are selected, the skin is disinfected, a peripheral venous infusion pathway is established, and the puncture needle is fixed. The infusion bag is hung on the infusion stand, the drip speed is adjusted, and the liquid medicine is infused into the human blood vessels. The pressure difference generated by venous pressure in the human body is generally maintained at 60-100 cm water column, so that liquid is ensured to naturally flow into the human body under the effect of pressure difference. During the infusion process, it is necessary to prevent failure of the operation such as the puncture needle coming out of vessels or falling off, and maintaining aseptic conditions during the process.

Bone marrow cavity infusion is a new technique for rapidly establishing vascular access. The puncture needle with a needle core penetrates into the bone marrow cavity of a long bone or the bone marrow cavity of the sternum through a special device, then the needle core is taken out, the connector is connected, and then the infusion device is connected, so that liquid is continuously infused into the bone marrow cavity. Clinically, infusion is often applied to the rescue treatment of a patient in shock. Because a patient in shock is often severely deficient in blood volume, the rescue of the patient is often affected because of unsuccessful venipuncture. At that time, infusion through the bone marrow cavity can quickly establish an infusion path, and a large amount of liquid and rescue drugs can be continuously infused into the bone marrow cavity of the patient and enter the blood circulation of the human body from the bone marrow cavity. Therefore, the purpose of rescuing patients is achieved.

In wars in frigid highland zones, the wounded patients in shock need immediate infusion rescue in the field and supplementation of lost blood to raise the blood pressure. According to the traditional method, saline and drugs are rapidly infused by establishing the peripheral venous access, and valuable rescue time is saved for the wounded that are in shock. The traditional peripheral vein puncture infusion device has the following problems during field infusion in frigid highland zones: firstly, the collapse of peripheral vessels is caused by shock, the position of peripheral vessels cannot be seen, and the puncture failure is caused by blind puncture; secondly, the infused liquid is free of a heating and heat preservation device, in a severely cold environment, the liquid becomes cold or even icy, causing stinging, chills, convulsion and other adverse symptoms after being infused into the body of the patient, and even the liquid cannot enter the human body at all after being icy; and thirdly, traditional infusion is free of a pressurizing device, and medical personnel in the field raise the infusion bags by hand for a long time during marching, resulting in unstable infusion and falling of the infusion device.

SUMMARY OF THE INVENTION

In order to solve the problems, the disclosure provides a field first-aid infusion device for frigid highland zones.

The technical scheme of the disclosure is realized as follows.

A field first-aid infusion device for frigid highland zones comprises a storage box, wherein a heat preservation and pressurization device, a marrow cavity puncture needle, a heat preservation infusion tube, a power-assisted puncture tool, a power supply and a power line are placed in the storage box, the heat preservation and pressurization device is electrically connected with the power supply through the power line, the heat preservation and pressurization device comprises a heating sleeve, magic tape is fixed to the surfaces of the two ends of the heating sleeve, a control box is fixed to the middle of the outer surface of the heating sleeve, the power line is inserted into the control box, at least one binding belt is fixed to the end, away from the magic tape, of the outer surface of the heating sleeve, the heating sleeve comprises a pressurizing air bag, a pressure sensor is fixed to one side of the pressurizing air bag in an adhesive mode, a tensile fabric layer is fixed to the other side of the pressurizing air bag, a first temperature sensor is embedded in the tensile fabric layer, a heat storage bag is fixed to one side of the tensile fabric layer, an electric heating wire is arranged on one side of the heat storage bag, a heat reflecting film is arranged on one side of the electric heating wire, a heat preservation sheath is arranged on one side of the heat reflecting film, waterproof cloth wraps the heat preservation sheath, the edges of the waterproof cloth, the heat preservation sheath, the heat reflecting film, the tensile fabric layer and the pressurizing air bag are fixed together, the electric heating wire and the heat storage bag are wrapped between the heat reflecting film and the tensile fabric layer, the electric heating wire and the first temperature sensor are electrically connected with the control box, the pressurizing air bag is connected with an air inlet pipe, the end of the air inlet pipe is connected with an inflating air bag, and a one-way valve is fixed to the air inlet pipe.

Further, a photovoltaic power generation panel is embedded in the outer wall of the storage box, and a power supply socket is fixed to the inner wall of the storage box.

Further, the heat preservation infusion tube comprises a PVC tube, a heat preservation sleeve is nested outside the PVC tube, a connector matched with the marrow cavity puncture needle is fixed at one end of the PVC tube, a second temperature sensor in contact with the outer wall of the PVC tube is embedded in the connector, the second temperature sensor is electrically connected with a quick connector, and a data line is fixed at the end of the quick connector and inserted into the control box.

Further, a flow rate regulator is arranged on the PVC tube, and the PVC tube and the heat preservation sleeve penetrate through the flow rate regulator.

Further, the power-assisted puncture tool comprises at least one of a manual puncture tool and an electric puncture tool.

Further, the power supply is any one of a hand-operated generator and a storage battery.

Further, a printed circuit board is fixed inside the control box, a single-chip microcomputer, a temperature controller and an alarm prompter are fixed on the printed circuit board, the temperature controller is electrically connected with the electric heating wire, a power jack and a data jack which are electrically connected with the printed circuit board are embedded in the side wall of the control box, the power jack is matched with the power line, the data jack is matched with the data line, status indicator lamps, a control switch and a human-computer interaction display screen are embedded in the outer surface of the control box, the temperature controller, the data jack, the alarm prompter and the human-computer interaction display screen are electrically connected with the single-chip microcomputer, and the control switch is connected in series between the power jack and the printed circuit board.

Further, the number of status indicator lamps is at least four, and the multiple status indicator lamps are respectively connected in series between the single-chip microcomputer and the temperature controller, between the single-chip microcomputer and the alarm prompter, between the control switch and the printed circuit board, and between the data jack and the printed circuit board.

Further, the alarm prompter is any one of a miniature vibration motor, a loudspeaker, an audible alarm, and a visual alarm or any combination thereof.

With the invention has the following beneficial effects: the use of bone marrow cavity puncture infusion/transfusion can avoid the occurrence of the phenomenon that a blood vessel cannot be found in the wounded during rescue in a cold environment; self-pressurization is realized by using the pressurizing air bag, so that the infusion/transfusion bag can be placed on the side of the wound or on the wound, hand-held elevation is not needed, and normal infusion/transfusion is ensured without relying on active power; heat can be applied to the drug/blood for heating and heat preservation, and the temperature can be automatically adjusted to avoid stinging, convulsion and other adverse symptoms caused by the infusion of cold liquid into the wounded; through controlled heating and pressurization, the wounded can get timely infusion/transfusion in the field in frigid highland zones, so that valuable rescue time is saved, meanwhile, the comfort of the wounded during treatment is reduced, the work of medical staff is alleviated, and a new channel is create for first-aid infusion of the wounded in shock under field conditions in frigid highland zones.

BRIEF DESCRIPTION OF THE DRAWINGS

To describe the technical solutions in the embodiments of the disclosure or in the prior art more clearly, the following briefly describes the attached figures required for describing the embodiments or the prior art. Apparently, the attached figures in the following description show some embodiments of the disclosure, and a person of ordinary skill in the art may still derive other attached figures from these attached figures without creative efforts.

Reference signs in the attached figures are as follows:

1, storage box; 2, photovoltaic power generation panel; 3, heat preservation and pressurization device; 31, heating sleeve; 311, waterproof cloth; 312, heat preservation sheath; 313, heat reflecting film; 314, electric heating wire; 315, heat storage bag; 316, tensile fabric layer; 317, pressurizing air bag; 318, first temperature sensor; 319, pressure sensor; 32, magic tape; 33, air inlet pipe; 34, control box; 341, printed circuit board; 342, single-chip microcomputer; 343, temperature controller; 344, power jack; 345, data jack; 346, alarm prompter; 347, status indicator lamp; 348, control switch; 349, human-computer interaction display screen; 35, one-way valve; 36, inflating air bag; 37, binding belt; 4, marrow cavity puncture needle; 5, heat preservation infusion tube; 51, PVC tube; 52, heat preservation sleeve; 53, connector; 54, second temperature sensor; 55, quick connector; 56, data line; 57, flow rate regulator; 6, power-assisted puncture tool; 7, power supply; and 8, power line.

DETAILED DESCRIPTION OF THE PREFERRED EMBODIMENTS

The following describes the technical scheme in the embodiments of the disclosure with reference to the attached figures. The described embodiments are merely a part rather than all of the embodiments of the disclosure. Based on the embodiment in the disclosure, all other embodiments obtained by one of the ordinary skill in the art without undue experimentation belong to the scope protected by the disclosure.

Figure 1:
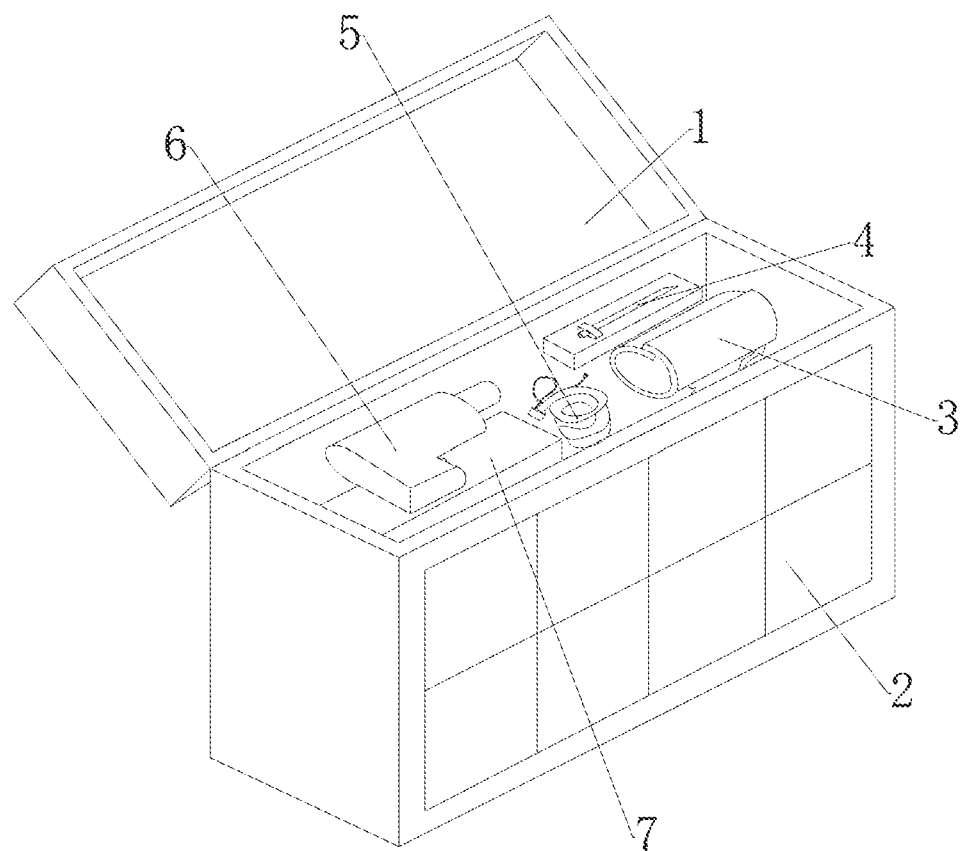
FIG. 1 is a schematic diagram of the disclosure.
Figure 2:
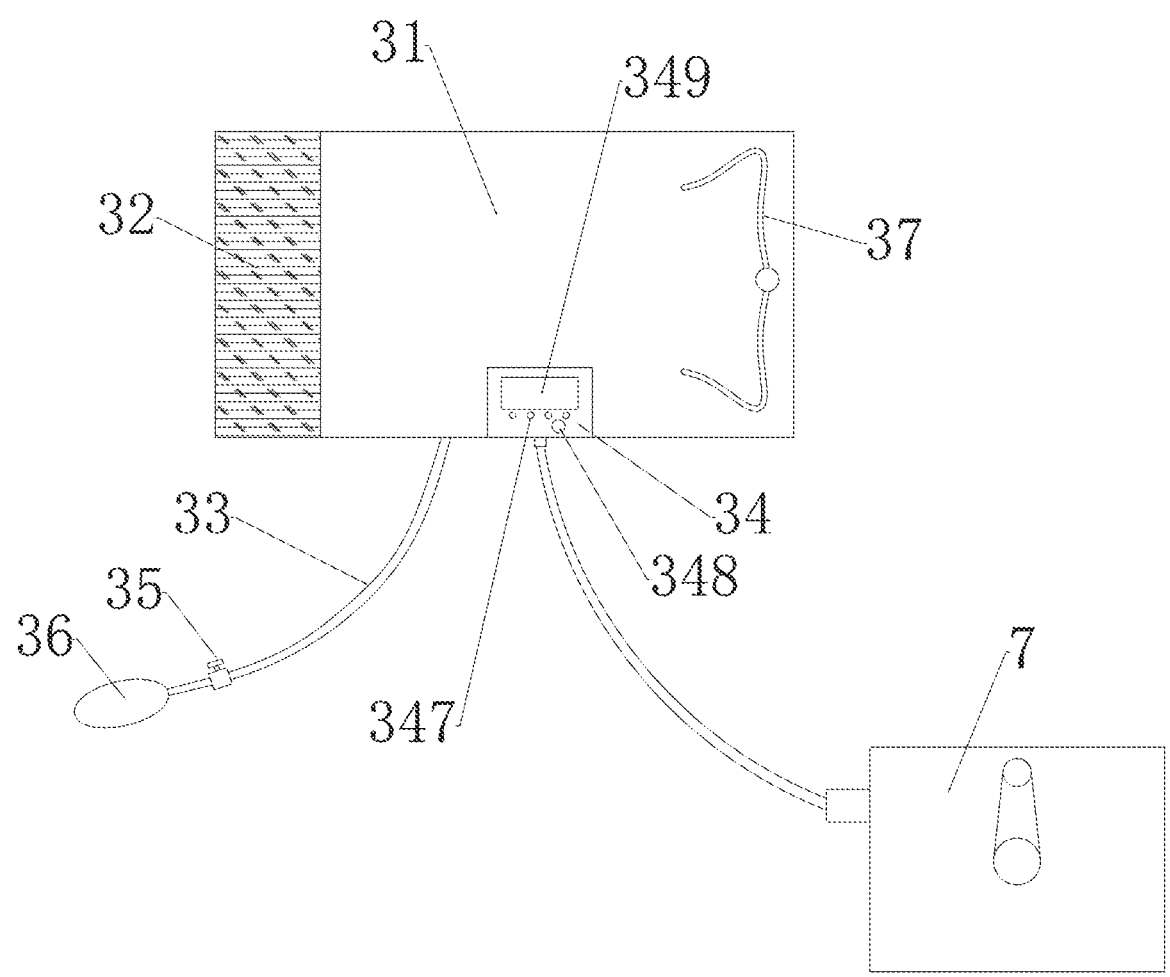
FIG. 2 is a front view of a heat preservation and pressurization device of the disclosure.
Figure 3:
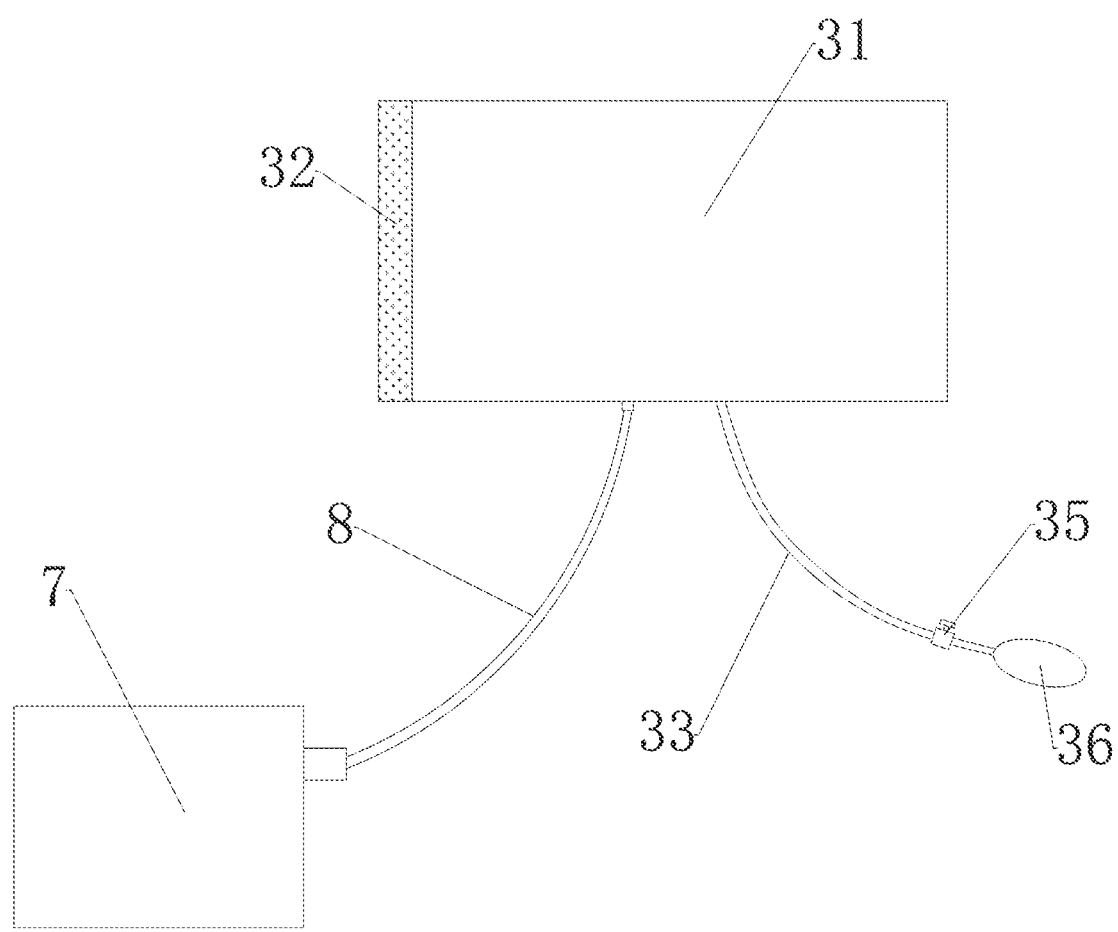
FIG. 3 is a rear view of a heat preservation and pressurization device of the disclosure.
Figure 4:
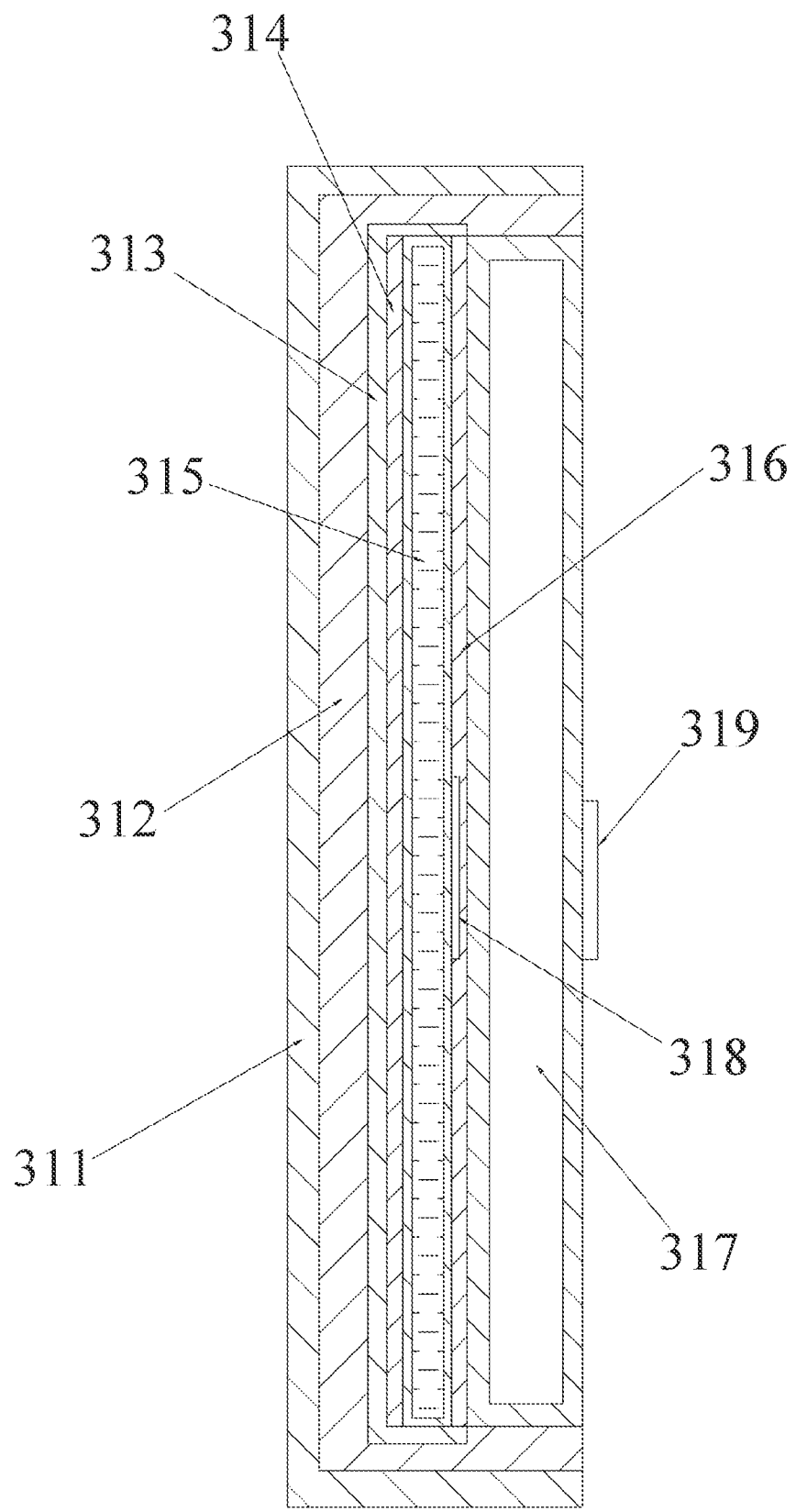
FIG. 4 is a sectional view of a heating sleeve of the disclosure.
Figure 5:
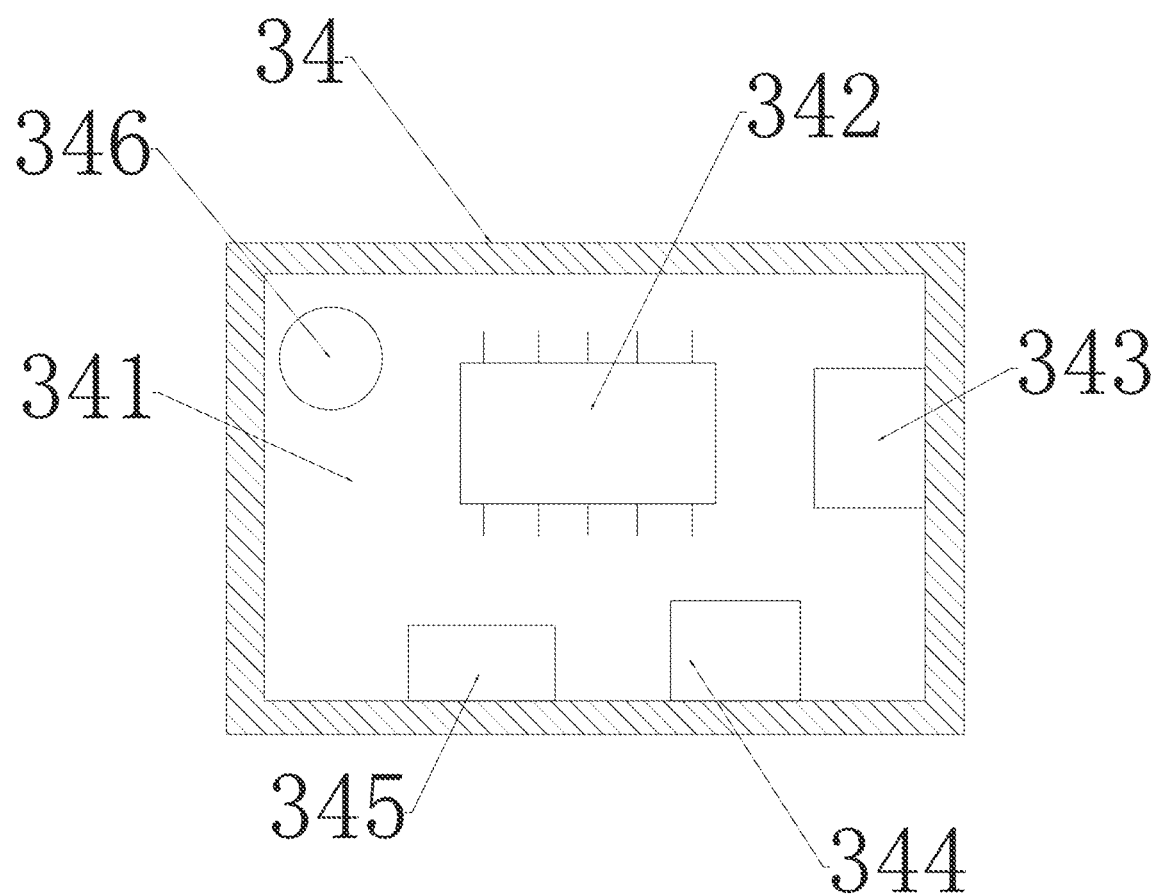
FIG. 5 is a sectional view of a control box of the disclosure.
Figure 6:
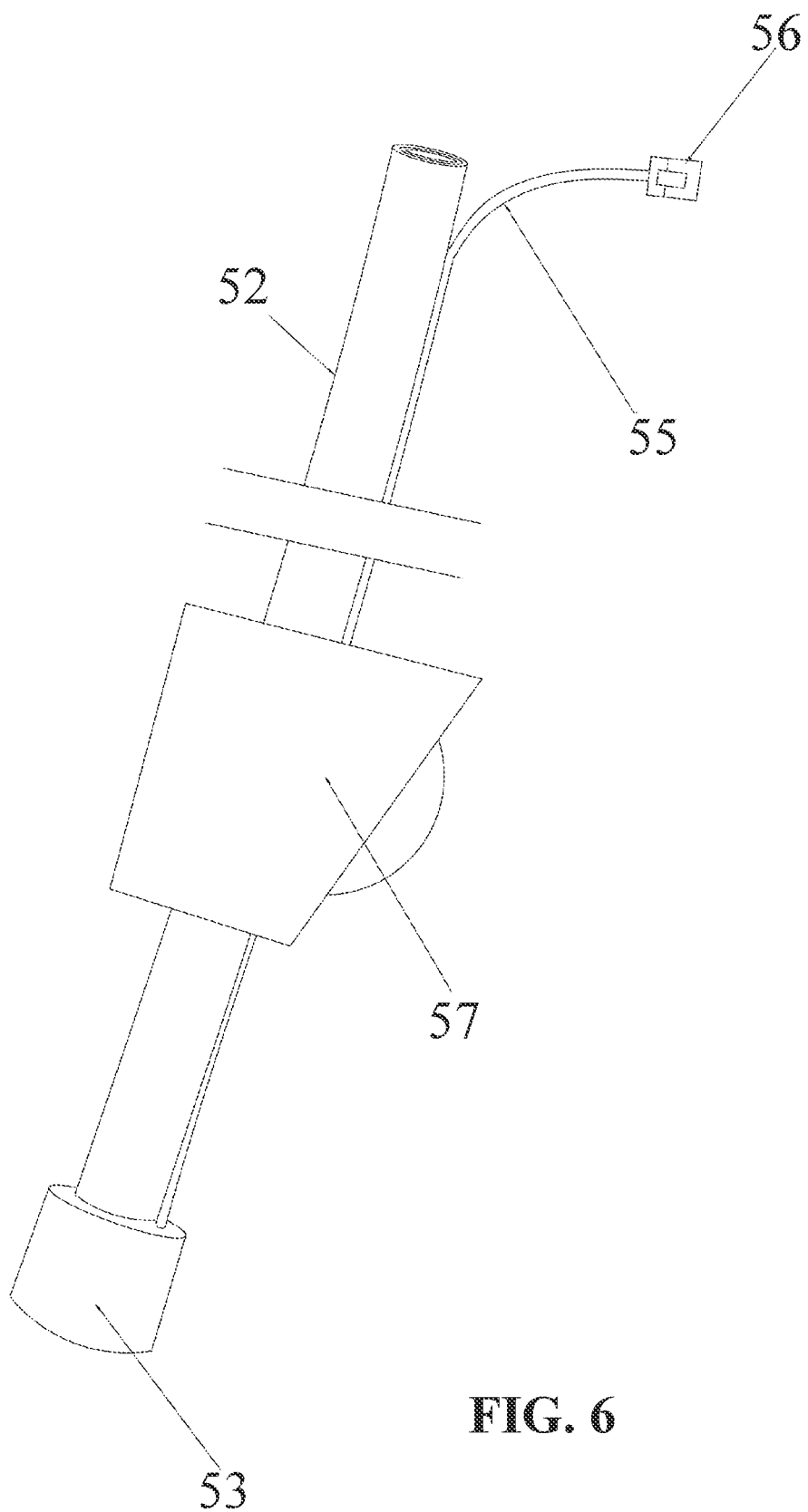
FIG. 6 is a schematic diagram of a heat preservation infusion tube of the disclosure.
Figure 7:
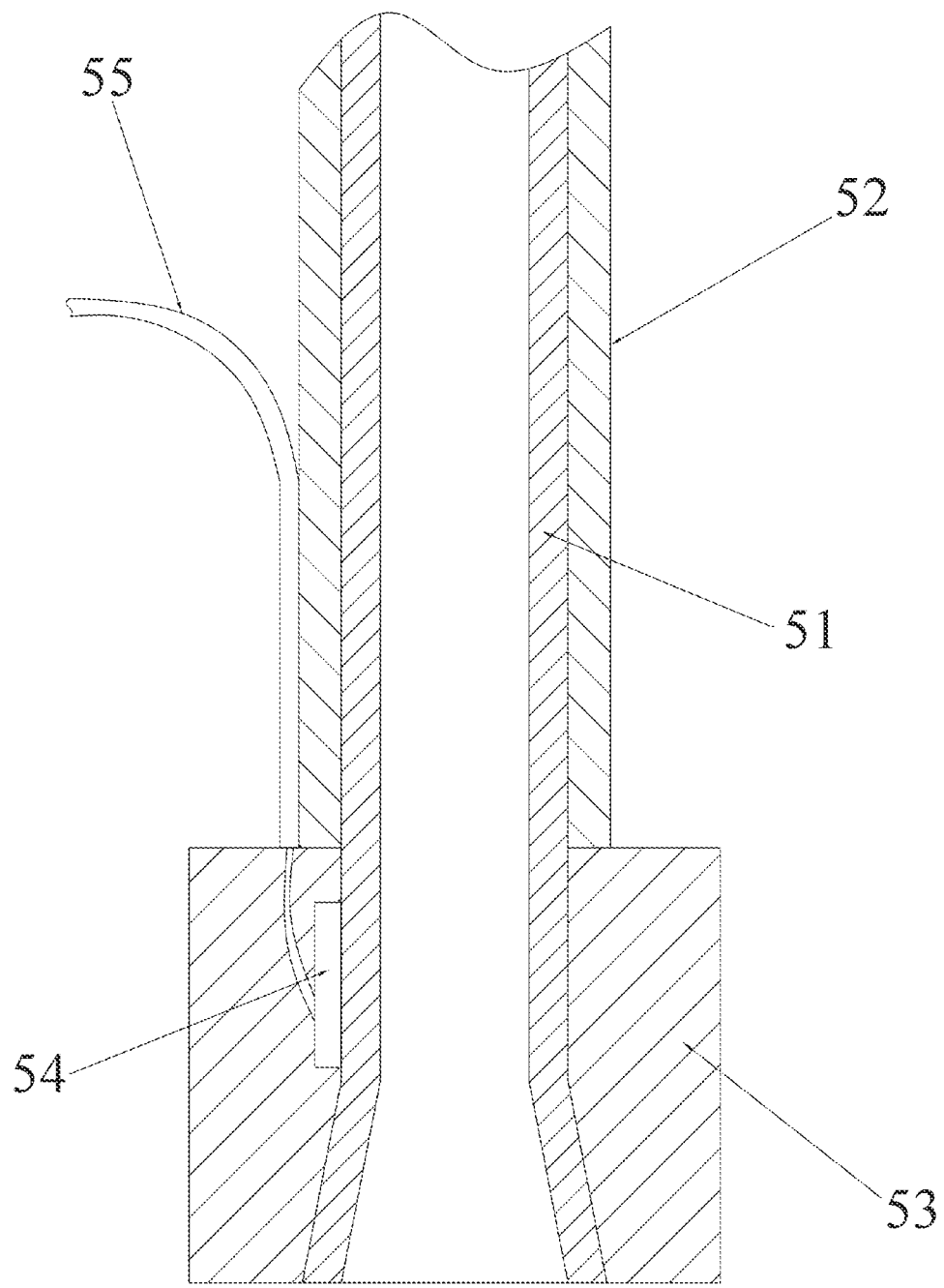
FIG. 7 is a partial sectional view of a heat preservation infusion tube of the disclosure.
Figure 8:
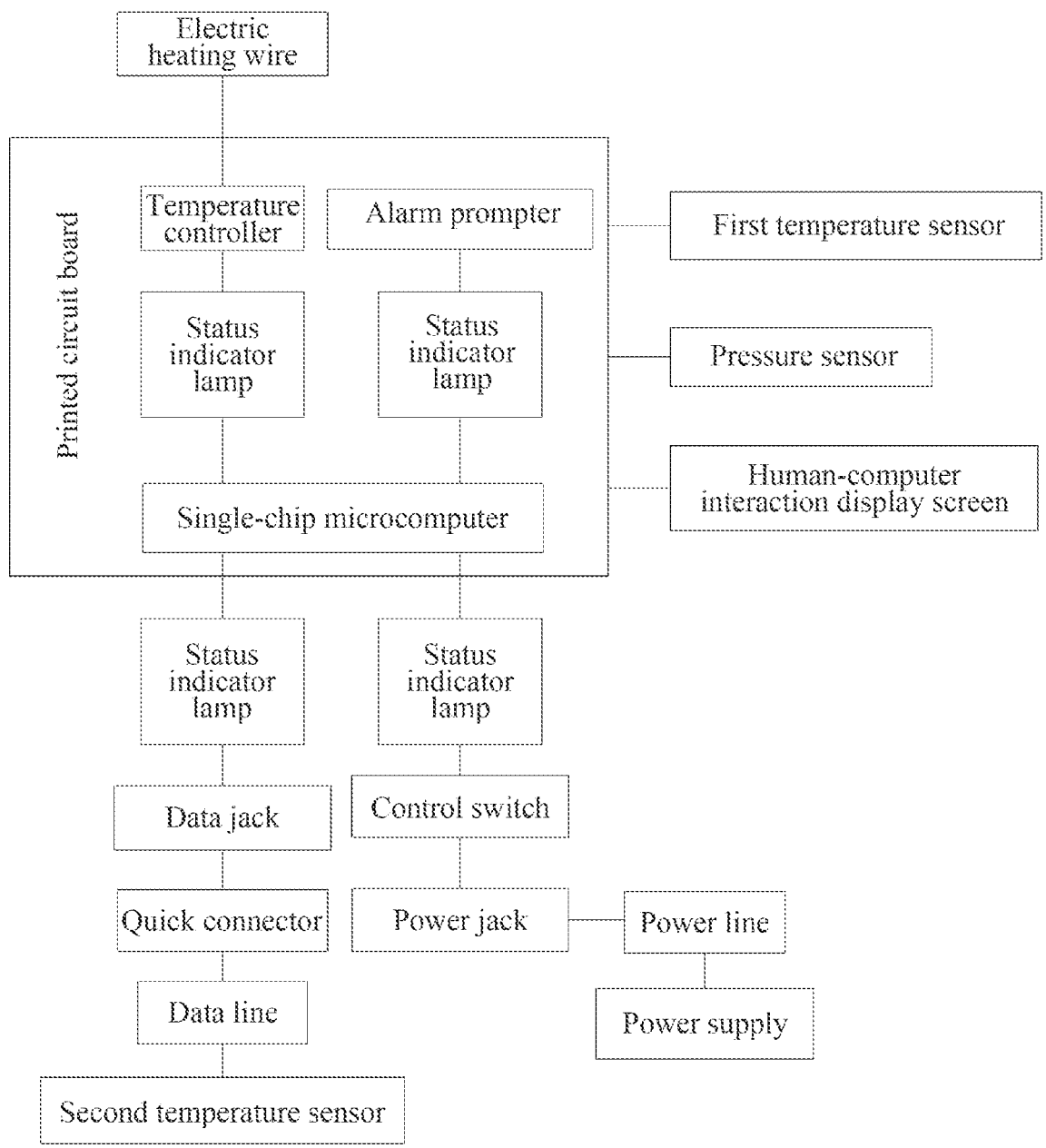
FIG. 8 is a schematic diagram of a circuit of the disclosure.

As shown in FIG. 1 to FIG. 8, a field first-aid infusion device for frigid highland zones comprises a storage box 1. The size of the storage box 1 may be similar to that of a first-aid backpack medical kit, so that the storage box 1 is convenient to carry. A photovoltaic power generation panel 2 is embedded in the outer wall of the storage box 1. Light energy can be used for power generation, so that the temporary power utilization requirement is guaranteed. A power supply socket is fixed to the inner wall of the storage box 1, and electronic equipment can be conveniently charged, so that it is guaranteed that power can be constantly supplied for use, and pollution caused by disposable batteries is relieved. A heat preservation and pressurization device 3, a marrow cavity puncture needle 4, a heat preservation infusion tube 5, a power-assisted puncture tool 6, a power supply 7 and a power line 8 are placed in the storage box 1. The heat preservation and pressurization device 3 is electrically connected with the power supply 7 through the power line 8. The power supply 7 is used for supplying power. The heat preservation and pressurization device 3 is used for heating and heat preservation of an infusion/transfusion bag. The heat preservation and pressurization device 3 comprises a heating sleeve 31. Magic tape 32, other hook-and-loop or suitable fastener, is fixed to the surfaces of the two ends of the heating sleeve 31, so that the heating sleeve 31 is conveniently fixed to the outside of the infusion/transfusion bag. A control box 34 is fixed to the middle of the outer surface of the heating sleeve 31. The power line 8 is inserted into the control box 34. At least one binding belt 37 is fixed to the end, away from the magic tape 32, of the outer surface of the heating sleeve 31. The binding belt 37 is used for binding and fixing, so that the magic tape 32 can be prevented from being separated when the pressurizing air bag 317 is inflated and expanded. The heating sleeve 31 comprises a pressurizing air bag 317. The pressurizing air bag 317 is in contact with the infusion/transfusion bag, so that it is guaranteed that pressure can be directly transmitted to the liquid in the infusion/transfusion bag. The pressure can be generally maintained at about 60-90 cm water column (similar to the pressure difference generated by liquid on an infusion support during extracorporeal venous infusion), so that it is guaranteed that the liquid can smoothly enter the marrow cavity and then enter the blood system of a human body. A pressure sensor 319 is fixed to one side of the pressurizing air bag 317 by an adhesive. In one embodiment, the preferred model of the pressure sensor 319 is BF350-3AA, and the pressure sensor 319 is used for detecting the magnitude of pressure applied to the infusion/transfusion bag after the pressurizing air bag 317 is expanded. A tensile fabric layer 316 is fixed to the other side of the pressurizing air bag 317.The tensile fabric layer 316 is made of high-strength fibers such as carbon fibers, high in strength and provided with a tensile performance cavity, so that the tensile fabric layer 316 is prevented from being driven to stretch and deform when the pressurizing air bag 317 is expanded, and pressure generated when the pressurizing air bag 317 is expanded is transmitted to the transfusion/transfusion bag. A first temperature sensor 318 is embedded in the tensile fabric layer 316. The model of the first temperature sensor 318 is preferably PT100, and the first temperature sensor 318 is used for detecting the temperature of the surface of the heat storage bag 315. A heat storage bag 315 is fixed to one side of the tensile fabric layer 316. Heat conduction oil is stored in the heat storage bag 315, and heat transfer is fast, so that heat can be absorbed and continuously released. The heat storage bag 315 has better heating and heat preservation effects, so that it is guaranteed that heat can still be continuously dissipated after power failure, and it is guaranteed that the temperature of the liquid in the infusion/transfusion bag is still within the desired range (25-37° C.) suitable for the human body for about one hour. An electric heating wire 314 is arranged on one side of the heat storage bag 315. A heat reflecting film 313 is arranged on one side of the electric heating wire 314. The heat reflecting film 313 is made of tinfoil and used for reflecting heat and reducing heat loss. A heat preservation sheath 312 is arranged on one side of the heat reflecting film 313. The heat preservation sheath 312 is made of cotton, down feather, silk floss and the like and used for heat preservation. Waterproof cloth 311 wraps the heat preservation sheath 312 and is used for water resistance. The edges of the waterproof cloth 311, the heat preservation sheath 312, the heat reflecting film 313, the tensile fabric layer 316 and the pressurizing air bag 317 are fixed together. The electric heating wire 314 and the heat storage bag 315 are wrapped between the heat reflecting film 313 and the tensile fabric layer 316, to guarantee that heat is conducted, and any electric leakage is prevented. The electric heating wire 314 and the first temperature sensor 318 are electrically connected with the control box 34. The pressurizing air bag 317 is connected with an air inlet pipe 33. The end of the air inlet pipe 33 is connected with an inflating air bag 36. A one-way valve 35 is fixed to the air inlet pipe 33. A deflation knob is arranged on the one-way valve 35, and air can be inflated into the pressurizing air bag 317 by extruding the inflating air bag 36 to expand the pressurizing air bag 317.

A printed circuit board 341 is fixed inside the control box 34. A single-chip microcomputer 342, a temperature controller 343 and an alarm prompter 346 are fixed on the printed circuit board 341. The model of the single-chip microcomputer 342 is preferably 80c51, and the single-chip microcomputer 342 is used for processing signals. The temperature controller 343 is electrically connected with the electric heating wire 314 and used for adjusting the heating temperature of the electric heating wire 314. A power jack 344 and a data jack 345 which are electrically connected with the printed circuit board 341 are embedded in the side wall of the control box 34. The power jack 344 is matched with the power line 8. The data jack 345 is matched with the data line 56. Status indicator lamps 347, a control switch 348 and a human-computer interaction display screen 349 are embedded in the outer surface of the control box 34. The status indicator lamps 347 are used for displaying working statuses. The human-computer interaction display screen 349 is preferably a touch display screen and used for displaying data and adjusting parameters through touch. The temperature controller 343, the data jack 345, the alarm prompter 346, the human-computer interaction display screen 349 are electrically connected with the single-chip microcomputer 342. The control switch 348 is connected in series between the power jack 344 and the printed circuit board 341 and used for controlling the on and off of a circuit. The number of the status indicator lamps 347 is at least four. The multiple status indicator lamps 347 are respectively connected in series between the single-chip microcomputer 342 and the temperature controller 343, between the single-chip microcomputer 342 and the alarm prompter 346, between the control switch 348 and the printed circuit board 341, and between the data jack 345 and the printed circuit board 341. The alarm prompter 346 is any one of a miniature vibration motor, a loudspeaker, and an audible and visual alarm and used for sending out a prompt signal.

The heat preservation infusion tube 5 comprises a PVC tube 51. A heat preservation sleeve 52 is nested outside the PVC tube 51 and is used for carrying out heat preservation on the liquid flowing in the PVC tube 51 and reducing heat loss. A connector 53 matched with the marrow cavity puncture needle 4 is fixed at one end of the PVC tube 51. A second temperature sensor 54 in contact with the outer wall of the PVC tube 51 is embedded in the connector 53. The model of the second temperature sensor 54 is preferably PT100, and the second temperature sensor 54 is used for detecting the temperature of the liquid entering the human body. The second temperature sensor 54 is electrically connected with a quick connector 55. A data line 56 is fixed at the end of the quick connector 55 and inserted into the control box 34. A flow rate regulator 57 is arranged on the PVC tube 51 and used for regulating the speed of flow rate. The PVC tube 51 and the heat preservation sleeve 52 penetrate through the flow rate regulator 57.

The power-assisted puncture tool 6 comprises at least one of a manual puncture tool and an electric puncture tool. The power-assisted puncture tool 6 is used for puncturing and drilling a hole on the human body so as to insert the marrow cavity puncture needle 4 into the marrow cavity.

The power supply 7 is any one of a hand-operated generator and a storage battery, and may be provided with a hand-operated generator and a storage battery at the same time. Firstly, electric energy generated by the photovoltaic power generation panel 2 can be used for supplying power, and then the hand-operated generator is used for power generation and heat production. A standby storage battery is not used when the electric supply is sufficient.

In the working principle of the device, when first aid is performed, for those who fail to perform intravenous puncture three times, intravenous infusion is no longer selected, but intramedullary puncture infusion is used instead. The heating sleeve 31 wraps the infusion/transfusion bag, and the heat preservation infusion tube 5 is connected well. The power line 8 is inserted between the heat preservation and pressurization device 3 and the power line 8. The heating temperature can be set through the human-computer interaction display screen 349 after the control switch 348 is started, and then the power-assisted puncture tool 6 is used for drilling a hole at a puncture point of a designated part of the human body. After air in the heat preservation infusion tube 5 is discharged, the marrow cavity puncture needle 4 is fixed in the puncture hole. The inflating air bag 36 is manually squeezed so that external air rapidly enters the pressurizing air bag 317 to inflate and expand the pressurizing air bag 317. The pressurizing air bag 317 squeezes the infusion/transfusion bag so that the liquid in the infusion/transfusion bag flows into the marrow cavity of the human body through the PVC tube 51. The pressure sensor 319 can detect the pressure generated to the infusion/transfusion bag when the pressurizing air bag 317 is inflated. The pressure value is displayed on the human-computer interaction display screen 349. When the pressure is insufficient, the inflating air bag 36 is manually squeezed again to inflate. The heat conduction oil is stored in the heat storage bag 315. The first temperature sensor 318 is used for detecting the temperature of the surface of the heat storage bag 315. The heat generated by the electric heating wire 314 is absorbed by the heat conduction oil stored in the heat storage bag 315 and then is emitted to heat the infusion/transfusion bag wrapped in the heating sleeve 31. The heated liquid flows into the human body through the PVC tube 51. The second temperature sensor 54 detects the temperature of the liquid when entering the marrow cavity puncture needle 4 and transmits data to the single-chip microcomputer 342. The single-chip microcomputer 342 sends a signal to the temperature controller 343 according to the detection data of the second temperature sensor 54 to adjust the heating temperature of the electric heating wire 314.

Meanwhile, the pressurizing air bag 317 and the electric heating wire 314 can be replaced with a warming and pressurizing infusion pump, so that the consumption of electric energy is increased, but the output pressure is stable.

The foregoing descriptions are merely exemplary embodiments of the disclosure but are not intended to limit the disclosure. Any modification, equivalent replacement, or improvement made within the spirit and principle of the disclosure shall fall within the protection scope of the disclosure.

What is claimed is:

1. A field first-aid infusion device for frigid highland zones, comprising a storage box, comprising a heat preservation and pressurization device, a marrow cavity puncture needle, a heat preservation infusion tube, a power-assisted puncture tool, a power supply and a power line, wherein the heat preservation and pressurization device is electrically connected with the power supply through the power line, the heat preservation and pressurization device comprises a heating sleeve, tape is fixed to surfaces of two ends of the heating sleeve, a control box is fixed to a middle of the outer surface of the heating sleeve, the power line is inserted into the control box, at least one binding belt is fixed to an end, away from the tape, of an outer surface of the heating sleeve, the heating sleeve comprises a pressurizing air bag, a pressure sensor is adhesively fixed to one side of the pressurizing air bag, a tensile fabric layer is fixed to the other side of the pressurizing air bag, a first temperature sensor is embedded in the tensile fabric layer, a heat storage bag is fixed to one side of the tensile fabric layer, an electric heating wire is arranged on one side of the heat storage bag, a heat reflecting film is arranged on one side of the electric heating wire, a heat preservation sheath is arranged on one side of the heat reflecting film, the heat preservation sheath is wrapped with waterproof cloth, edges of the waterproof cloth, the heat preservation sheath, the heat reflecting film, the tensile fabric layer and the pressurizing air bag are fixed together, the electric heating wire and the heat storage bag are wrapped between the heat reflecting film and the tensile fabric layer, the electric heating wire and the first temperature sensor are electrically connected with the control box, the pressurizing air bag is connected with an air inlet pipe, an end of the air inlet pipe is connected with an inflating air bag, and a one-way valve is fixed to the air inlet pipe.

2. The field first-aid infusion device for frigid highland zones according to claim 1, wherein a photovoltaic power generation panel is embedded in an outer wall of the storage box, and a power supply socket is fixed to an inner wall of the storage box.

3. The field first-aid infusion device for frigid highland zones according to claim 1, wherein the heat preservation infusion tube comprises a PVC tube, a heat preservation sleeve is nested outside the PVC tube, a connector matched with the marrow cavity puncture needle is fixed at one end of the PVC tube, a second temperature sensor in contact with the outer wall of the PVC tube is embedded in the connector, the second temperature sensor is electrically connected with a quick connector, and a data line is fixed at an end of the quick connector and inserted into the control box.

4. The field first-aid infusion device for frigid highland zones according to claim 3, wherein a flow rate regulator is arranged on the PVC tube, and the PVC tube and the heat preservation sleeve penetrate through the flow rate regulator.

5. The field first-aid infusion device for frigid highland zones according to claim 1, wherein the power-assisted puncture tool comprises at least one of a manual puncture tool and an electric puncture tool.

6. The field first-aid infusion device for frigid highland zones according to claim 1, wherein the power supply is a hand-operated generator or a storage battery.

7. The field first-aid infusion device for frigid highland zones according to claim 1, wherein a printed circuit board is fixed inside the control box, a single-chip microcomputer, a temperature controller and an alarm prompter are fixed on the printed circuit board, the temperature controller is electrically connected with the electric heating wire, a power jack and a data jack which are electrically connected with the printed circuit board are embedded in a side wall of the control box, the power jack is matched with the power line, the data jack is matched with the data line, status indicator lamps, a control switch and a human-computer interaction display screen are embedded in an outer surface of the control box, the temperature controller, the data jack, the alarm prompter and the human-computer interaction display screen are electrically connected with the single-chip microcomputer, and the control switch is connected in series between the power jack and the printed circuit board.

8. The field first-aid infusion device for frigid highland zones according to claim 7, wherein the number of the status indicator lamps is at least four, and the at least four status indicator lamps are respectively connected in series between the single-chip microcomputer and the temperature controller, between the single-chip microcomputer and the alarm prompter, between the control switch and the printed circuit board, and between the data jack and the printed circuit board.

9. The field first-aid infusion device for frigid highland zones according to claim 7, wherein the alarm prompter is a miniature vibration motor, a loudspeaker, or an audible and visual alarm.

* * * * *